(12) United States Patent
Miccio et al.

(10) Patent No.: US 11,865,014 B2
(45) Date of Patent: Jan. 9, 2024

(54) SURFACE TREATED MEDICAL IMPLANT DEVICES

(71) Applicant: GLOBUS MEDICAL, INC., Audubon, PA (US)

(72) Inventors: Mark Miccio, Lynbrook, NY (US); Jason Zappacosta, Philadelphia, PA (US)

(73) Assignee: Globus Medical, Inc, Audubon, PA (US)

( * ) Notice: Subject to any disclaimer, the term of this patent is extended or adjusted under 35 U.S.C. 154(b) by 275 days.

(21) Appl. No.: 17/494,287

(22) Filed: Oct. 5, 2021

(65) Prior Publication Data

US 2022/0023064 A1 Jan. 27, 2022

Related U.S. Application Data

(63) Continuation of application No. 16/600,975, filed on Oct. 14, 2019, now Pat. No. 11,166,824, which is a
(Continued)

(51) Int. Cl.
*A61F 2/44* (2006.01)
*A61F 2/30* (2006.01)
(Continued)

(52) U.S. Cl.
CPC .......... *A61F 2/4455* (2013.01); *A61F 2/0077* (2013.01); *A61F 2/30771* (2013.01); *A61L 27/50* (2013.01); *A61L 27/56* (2013.01); *A61L 31/14* (2013.01); *A61L 31/146* (2013.01); *A61F 2002/0081* (2013.01); *A61F 2002/3092* (2013.01); *A61F 2002/30092* (2013.01); *A61F 2002/3093* (2013.01); *A61F 2002/30538* (2013.01); *A61F 2002/30593* (2013.01); *A61F 2002/30784* (2013.01);
(Continued)

(58) Field of Classification Search
CPC .............................. A61F 2/4455; A61F 2/0077
See application file for complete search history.

(56) References Cited

U.S. PATENT DOCUMENTS

| 4,522,656 A | 6/1985 | Kuhn-Kuhnenfeld et al. |
| 4,673,409 A | 6/1987 | Van Kampen |

(Continued)

FOREIGN PATENT DOCUMENTS

| EP | 3443992 A1 | 8/2018 |
| JP | H04246360 A | 9/1992 |

(Continued)

OTHER PUBLICATIONS

Muller, "Effect of Surface Finish on the osseointegration of Laser-Treated Titanium Alloy Implants", Nov. 8, 2003, 4057-4064; Biomaterials, 25 (2004), Elsevier.

(Continued)

*Primary Examiner* — Christian A Sevilla

(57) ABSTRACT

A surgical implant having a surface treatment which contains primary cavities and secondary cavities. The primary cavities are larger than the secondary cavities and the primary cavities have an average length ranging from 20-500 micrometers. The surface treatment includes recasted material adjacent to a plurality of the primary cavities.

17 Claims, 12 Drawing Sheets

Related U.S. Application Data continuation of application No. 15/675,864, filed on Aug. 14, 2017, now Pat. No. 10,478,311.

(51) Int. Cl.

| | |
|---|---|
| *A61L 27/56* | (2006.01) |
| *A61L 31/14* | (2006.01) |
| *A61F 2/00* | (2006.01) |
| *A61L 27/50* | (2006.01) |
| *A61F 2/46* | (2006.01) |

(52) U.S. Cl.
CPC .............. *A61F 2002/30836* (2013.01); *A61F 2002/30838* (2013.01); *A61F 2002/30925* (2013.01); *A61F 2002/4629* (2013.01); *A61F 2310/00017* (2013.01); *A61F 2310/00023* (2013.01); *A61F 2310/00029* (2013.01); *A61F 2310/00059* (2013.01); *A61F 2310/00095* (2013.01); *A61L 2400/18* (2013.01); *A61L 2430/02* (2013.01); *A61L 2430/38* (2013.01)

(56) References Cited

U.S. PATENT DOCUMENTS

| | | | |
|---|---|---|---|
| 4,865,603 A | 9/1989 | Noiles | |
| 4,964,801 A | 10/1990 | Kawahara et al. | |
| 5,062,021 A | 10/1991 | Ranjan et al. | |
| 5,108,781 A | 4/1992 | Ranjan et al. | |
| 5,246,530 A | 9/1993 | Bugle et al. | |
| 5,607,607 A | 3/1997 | Naiman et al. | |
| 5,645,740 A | 7/1997 | Naiman et al. | |
| 5,665,118 A * | 9/1997 | LaSalle | B33Y 10/00 623/23.5 |
| 5,713,410 A | 2/1998 | LaSalle et al. | |
| 5,716,412 A | 2/1998 | DeCarlo, Jr. et al. | |
| 5,843,289 A | 12/1998 | Lee et al. | |
| 5,863,201 A * | 1/1999 | Lazzara | B24C 11/00 433/199.1 |
| 5,876,453 A | 3/1999 | Beaty | |
| 5,910,173 A | 6/1999 | DeCarlo, Jr. et al. | |
| 5,965,006 A * | 10/1999 | Baege | A61L 27/34 205/685 |
| 6,005,164 A | 12/1999 | Johansson et al. | |
| 6,419,491 B1 | 7/2002 | Ricci et al. | |
| 6,527,938 B2 | 3/2003 | Bales et al. | |
| 6,652,765 B1 | 11/2003 | Beaty | |
| 6,969,474 B2 | 11/2005 | Beaty | |
| 6,974,482 B2 | 12/2005 | Zhu | |
| 7,090,494 B2 | 8/2006 | Shelemay et al. | |
| 7,205,230 B2 | 4/2007 | Mashino | |
| 7,258,810 B2 | 8/2007 | Hunter et al. | |
| 7,169,317 B2 | 11/2007 | Beaty | |
| 7,547,399 B2 | 6/2009 | Beaty | |
| 7,556,500 B2 | 7/2009 | Ihde | |
| 7,857,987 B2 | 12/2010 | Beaty | |
| 8,048,591 B2 | 11/2011 | Kasahara et al. | |
| 8,221,499 B2 | 7/2012 | Lazzara et al. | |
| 8,251,700 B2 | 8/2012 | Robb et al. | |
| 8,496,710 B2 | 7/2013 | Bagga et al. | |
| 8,758,442 B2 | 6/2014 | Ullrich, Jr. et al. | |
| 8,764,444 B2 | 7/2014 | Hansson | |
| 8,859,078 B2 | 10/2014 | Maurin-Perrier et al. | |
| 9,015,922 B2 | 4/2015 | Ganey | |
| 9,125,756 B2 * | 9/2015 | Ullrich, Jr. | C23C 14/34 |
| 9,179,954 B2 | 11/2015 | Ganey | |
| 9,241,810 B1 | 1/2016 | Rumi et al. | |
| 9,327,051 B2 | 5/2016 | Ullrich, Jr. et al. | |
| 9,408,711 B2 | 8/2016 | Burkinshaw et al. | |
| 9,433,511 B2 | 9/2016 | Bagga et al. | |
| 2001/0039454 A1 | 11/2001 | Ricci et al. | |
| 2006/0100716 A1 | 5/2006 | Lerf | |
| 2008/0154378 A1 | 6/2008 | Pelo | |
| 2009/0012611 A1 | 1/2009 | Brosnahan, III et al. | |
| 2009/0082810 A1 * | 3/2009 | Bhatnagar | A61B 17/701 606/103 |
| 2011/0112650 A1 | 5/2011 | Masini | |
| 2013/0282122 A1 | 10/2013 | Ullrich, Jr. et al. | |
| 2013/0306591 A1 | 11/2013 | Ullrich, Jr. et al. | |
| 2014/0094921 A1 | 4/2014 | Patterson et al. | |
| 2015/0018958 A1 | 1/2015 | Ulrich, Jr. et al. | |
| 2015/0335434 A1 | 11/2015 | Patterson et al. | |
| 2016/0100954 A1 | 4/2016 | Rumi et al. | |
| 2016/0331545 A1 | 11/2016 | Burkinshaw et al. | |
| 2018/0325646 A1 * | 11/2018 | Burke | A61L 33/06 |

FOREIGN PATENT DOCUMENTS

| | | |
|---|---|---|
| JP | H09504193 A | 4/1997 |
| JP | 2007504899 A | 3/2007 |
| WO | 2009046517 A1 | 4/2009 |
| WO | 2013142480 A1 | 9/2013 |
| WO | 2016148923 A1 | 9/2019 |

OTHER PUBLICATIONS

Bobyn et al., "The Optimum Pore Size for the Fixation of Porous-Surfaced Metal Implants by the Ingrowth of Bone", Basic Science and Pathology, Section III, Jul.-Aug. 1980, No. 150, pp. 263-270, J. B. Lippincott Co.

Dumas et al., "Multiscale grooved titanium processed with femtosecond laser", Journal of Biomedical Materials Research A, Nov. 2012, vol. 100A, Issue 11, pp. 3108-3116, Dec. 15, 2011.

Yang et al., "Recast layer removal using ultrafast laser in titanium alloy", Int J Adv Manuf Technol (2013) 68:2321-2327, Aug. 3, 2012.

Dumas et al. "Femtosecond lase non/micro paterning of titanium influences", "Biomedical Materials", Biomed. Mater. 10 (2015) 055002, 13 pages, Apr. 17, 2015.

* cited by examiner

SURFACE TREATED MEDICAL IMPLANT DEVICES

CROSS REFERENCE TO RELATED APPLICATIONS

This application is a continuation application of U.S. patent application Ser. No. 16/600,975 filed on Oct. 14, 2019 which is a continuation of U.S. patent application Ser. No. 15/675,864, filed on Aug. 14, 2017, which is incorporated herein in its entirety.

FIELD OF THE INVENTION

The present invention relates to new methods of surface treating implants, and implants having the new surface treatment. Such surface treatment improves the osseointegration of the implant.

BACKGROUND OF THE INVENTION

Implants which are inserted into mammals, such as people, have been utilized for a number of years. One of the most critical features of an implant is the osseointegration of the implant. Since implants are foreign objects in the body of a patient, it is important that the implants be fully integrated into the patient's body both structurally and functionally in order to provide the desired effect. This is done via osseointegration, where the formation of bone and supporting connective tissue grows up to the surface of the implant. In other words, the bone and the implant become "integrated" and the implant becomes part of the patient's body as if it had been there initially. For example, it is important for implants, such as spinal implants, to have good and timely osseointegration for maximum benefit to patients, especially to ensure that proper support to the spine and torso are provided by well-integrated implants that take the place of other structurally-supporting structures in the body. Thus, there is a need to better improve the osseointegration of implants, including spinal implants, hip implants and implants of the extremities, into the bodies of patients, in order to improve the stability and performance of the implant in a structural and functional capacity.

SUMMARY

In some embodiments, a surgical implant is provided comprising a body sized and configured to be inserted in a disc space. The body comprises an upper surface and a lower surface, wherein at least one of the upper surface and lower surface comprises a surface treatment which contains primary cavities and secondary cavities, whereby the primary cavities are larger than the secondary cavities. The primary cavities can have an average length ranging from 20-500 micrometers. Furthermore, the surface treatment can comprise recasted material adjacent to a plurality of the primary cavities.

In other embodiments, a surgical implant is provided comprising an implantable body formed at least in part of a metal sized and configured to be inserted in a disc space. The body comprises an upper surface and a lower surface, wherein at least one of the upper surface and the lower surface comprises a surface treatment which contains primary cavities and secondary cavities, whereby the primary cavities are larger than the secondary cavities. The primary cavities can have an average length ranging from 20-500 micrometers. Furthermore, the surface treatment comprises recasted material adjacent to a plurality of the primary cavities.

In other embodiments, a surgical implant is provided comprising an implantable body formed at least in part of a metal sized and configured to be inserted in a disc space. The body comprises an upper surface and a lower surface, wherein at least one of the upper surface and the lower surface comprises a surface treatment which contains primary cavities and secondary cavities, whereby the primary cavities are larger than the secondary cavities. Furthermore, the surface treatment comprises recasted material adjacent to a plurality of the primary cavities.

DETAILED DESCRIPTION OF THE INVENTION

As stated above, there is a need to improve the osseointegration of implants generally, especially spinal implants. The present invention addresses this issue by utilizing novel surface treatments comprising laser marking technology to form a roughened and/or porous surface on the implants. One skilled in the art will appreciate that the novel surface treatments described herein can be used for implants beyond spinal implants, including hip implants, implants of the extremities and any other implants that can benefit from improved osseointegration.

In some embodiments, there are a number of spinal implants in which the technology of the present application would be extremely beneficial. Those implants include, but are not limited to, expandable spacers; plate and spacer systems (stand-alone and otherwise); screw systems; occipito-cervico-thoracic stabilization systems; cervico-thoracic stabilization systems; spinous process fixation plates; and plate systems generally, including spinous process fixation plates. Examples of expandable spacers are described in the following U.S. patent application Ser. No. 13/963,720 (published as U.S. 2014/0249628); Ser. No. 14/199,594 (published as U.S. 2014/0303731); Ser. No. 14/179,178 (published as U.S. 2015/0051701); Ser. No. 14/694,087

(published as U.S. 2015/0282942); and Ser. No. 14/887,476 (published as U.S. 2016/0038305), all of which are incorporated by reference into this document for all their teachings and for all purposes. Examples of plate and spacer systems are described in the following U.S. patent application Ser. No. 14/727,035 (published as U.S. 2015/0335443); Ser. No. 13/408,188 (published as U.S. 2013/0226244); and Ser. No. 14/476,439 (published as U.S. 2016/0058565), all of which are incorporated by reference into this document for all their teachings and for all purposes. Examples of screw systems are described in the following U.S. patent application Ser. No. 15/193,289 (published as U.S. 2016/0302831) and Ser. No. 13/114,803 (published as U.S. 2012/0303063), all of which are incorporated by reference into this document for all their teachings and for all purposes. Examples of occipito occipito-cervico-thoracic stabilization systems are described in U.S. patent application Ser. No. 12/883,903 (published as U.S. 2012/0071926), all of which are incorporated by reference into this document for all their teachings and for all purposes. Examples of plate systems are described in the following U.S. patent application Ser. No. 14/875,731 (published as U.S. 2016/0022326) and Ser. No. 13/086,122 (published as U.S. 2012/0265203), all of which are incorporated by reference into this document for all their teachings and for all purposes.

Figure 4:
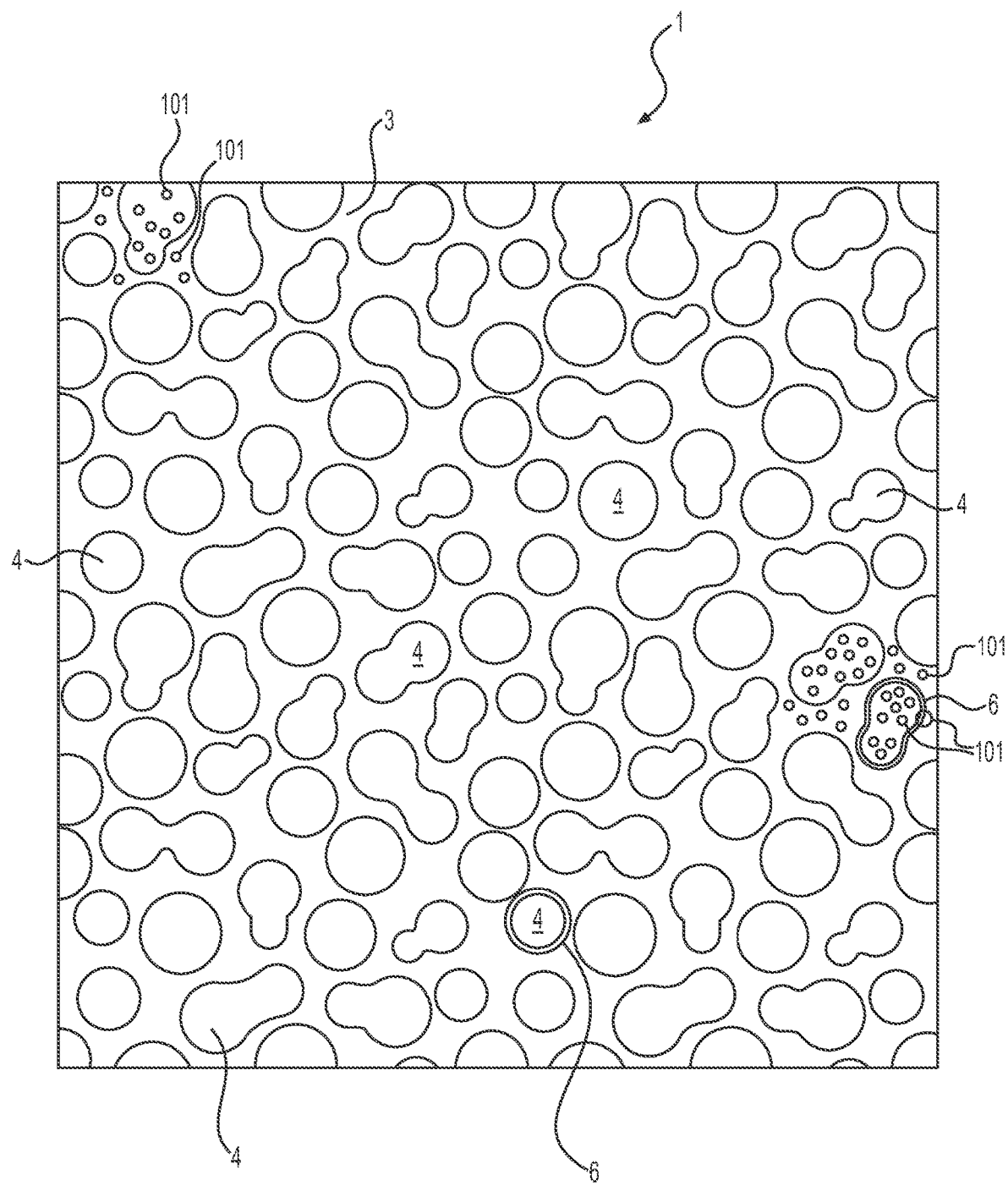
FIG. 4 shows a top view of the primary cavity pattern of the present invention.

In some embodiments, the above-identified implants have a novel surface treatment in at least a portion of their outer surface. In some embodiments, at least one of the above-identified implants is treated with lasers to impart the novel surface treatment of the present invention to at least a portion of the outer surface of the implants. In some embodiments, the novel surface treatment creates on an implantable surface a primary pattern of cavities and a secondary pattern of smaller cavities, as shown in FIG. 4, thereby promoting osseointegration.

The detailed description set forth below is intended as a description of some, but not all, of the configurations of the subject technology and is not intended to represent an exhaustive list. The detailed description includes specific details for the purpose of providing a thorough understanding of the present invention and subject technology. The subject invention and technology is not limited to the specific details set forth herein and may be practiced without these specific details. In other instances, well-known structures and techniques have not been shown or described in detail so as not to obscure the disclosure.

In the present invention, a novel surface treatment can be provided whereby laser pulses are used to deform the one or more surfaces of an implant to advantageously promote improved osseointegration. In some embodiments, multiple laser pulses create cavities, holes, voids, craters, pores, pits, and/or peaks having particular patterns of varying dimensions based upon the laser raster rate, peak power, travel pattern, and frequency. FIG. 4, for example, illustrates an implantable surface or substrate having patterns of primary cavities 4 and smaller secondary cavities 101 formed in and around the primary cavities 4. In some embodiments, a laser raster rate of between 1-4000 mm/s is used to create one or more patterns. In some embodiments, a laser raster rate of approximately 1-3000 mm/s is used to create one or more patterns. In other embodiments a laser raster rate of 2500 mm/s is used to create one or more patterns.

In some embodiments, the lasers will be used to treat a substrate, such as a surface of an implant. In some embodiments, the substrate can comprise a surface of an implant formed of a metal, such as one or more of the following: cobalt chrome, steel, titanium, a titanium alloy (such as a titanium-niobium alloy), titanium oxide, tantalum, niobium, nitinol, or any other implantable grade metal and/or alloy. In some embodiments, the lasers can be used to form cavities of distinct patterns that will promote osseointegration.

Cavity patterns can be formed/etched into the substrate via multiple laser pulse passes, or "slices", in order to promote osseointegration. In some embodiments, two patterns of cavities can be formed on a substrate—a primary cavity pattern with larger cavities and a secondary cavity pattern with smaller cavities. For example, FIG. 4 shows cavity patterns on a substrate wherein a primary cavity pattern with larger cavities 4 is formed along with smaller secondary cavities 101. In some embodiments, to save time, one pass can be used for the primary pattern and one pass can be used for the secondary pattern, whereby each pass would consist of firing one or more pulses to form each cavity. While the present application envisions this more efficient process, it may be desirable to fire more than one pulse at each location where a cavity is desired to make the desired cavity. In some embodiments, applying multiple pulses to form one or more cavities can advantageously improve the surface roughness of the substrate due the accumulation of recasted material around the cavities. More specifically, as the laser beams make contact with the substrate surface, such as a metal, some or all of the material is "recasted", which means that the targeted material is moved elsewhere by the laser. In some embodiments, if a single laser pulse is utilized to make one cavity, there would be one chunk of recasted material deposited adjacent to the cavity. By having multiple pulses, there are many smaller chunks of recasted material which are deposited adjacent to the cavity and are more likely to be more evenly distributed since the smaller chunks could be deposited at different locations around the perimeter of the cavity along the outer surface of the substrate. Additionally, having multiple passes reduces localized heating, as more fully explained below.

In order to reduce time and complexity, firing laser pulses on the same location to create a cavity prior to moving on to a different part of the substrate to create another cavity may be preferable. However, in some circumstances, firing laser pulses on a single location for too long can create unwanted localized heating, which can damage the implant. Thus, it has been found that a laser surface treatment whereby the laser does not get fired at the same cavity repeatedly and consecutively may be desired in some circumstances. Rather, in some embodiments, the laser makes one pass to form a set of small or shallow cavities in, for example, a row or other pattern. After a brief cooling period, the laser can then make another pass to enlarge or deepen the set of shallow cavities into deeper cavities by firing a laser at each cavity in a second pass. This process is repeated for a number of times until the desired cavity size or depth is achieved. This advantageously gives the substrate at and near each cavity time to cool in between laser passes to avoid the unwanted localized heating.

The above process can be used to form the primary and secondary cavities mentioned above and shown, for example, in FIG. 4. The formation of the primary cavities may require the predetermination of a primary pattern for cavity formation since the laser may make multiple passes to make the cavities and therefore the software which controls the laser would ensure that the laser is fired in the desired pattern for each pass. The primary cavities will form the primary cavity pattern, and the primary cavity pattern includes recasted material adjacent to the perimeter of primary cavities on the substrate surface. The recasted material will in many cases extend mostly or all the way around the perimeter of a primary cavity on the substrate surface. Thus, the metal would form recasted portions around the cavity from which it originated. The recasted material can build up on the original plane of the surface around the mouth of the cavities, increasing the effective peak-to-valley height of the topography.

In the present invention, two important objectives are met via the enhanced surface treatment described herein. First, the cavities in the metal surface have a target size and/or depth that meet functional requirements of osseointegration. Second, the amount of smooth surfaces on the substrate are reduced and transformed into rough surfaces that encourage the penetration of bone and are more visually pleasing.

With respect to the first objective, the primary cavities are important in this respect. In some embodiments, the primary cavity pattern can have cavities having an average target cavity diameter, or length, of 20 to 500 micrometers. More preferably, the average length of the primary cavities can be 50 to 450 micrometers. More preferably, the average length of the primary cavities can be 100 to 300 micrometers. Most preferably, the average length of the primary cavities can be 150 to 250 micrometers. Additionally, the primary cavity pattern can have primary cavities having an average net depth from peak to trough of about 20-500 micrometers. More preferably, the average net depth of the primary cavities can be 50 to 450 micrometers. More preferably, the average net depth of the primary cavities can be 100 to 300 micrometers. Even more preferably, the average net depth of the primary cavities can be 150 to 250 micrometers. Most preferably, the net depth of the primary cavities can be an average of 175-240 micrometers. The net depth extends from above the plane of the original surface to below the plane of the original surface since parts of the surface roughness are above the plane of the original surface due to the recasting of material. In other words, when the laser contacts the substrate, some of the substrate will vaporize and some of it will be recasted outside of the cavity proximate to the cavity.

In some embodiments, the primary cavity pattern can have primary cavities with an average etched depth (measured from the surface of the substrate) of between about 19-499 micrometers. More preferably, the average etched net depth of the primary cavities can be between about 50 to 350 micrometers. More preferably, the average etched depth of the primary cavities can be between about 75 to 290 micrometers. Even more preferably, the average etched depth of the primary cavities can be between about 90 to 240 micrometers. Even more preferably, the etched depth of the primary cavities can be an average of 95-190 micrometers. Most preferably, the etched depth of the primary cavities can be an average of about 110-180 micrometers. The etched depth refers to the distance from the original surface of the implant to the bottoms of the primary cavities. Appropriate laser power and frequency of pulses, as well as the raster rate, are utilized to obtain the desired etched depth and recasted material. In some embodiments, the recasted material can have an average height of 1-100 micrometers. More preferably, the recasted material can have an average height of about 25-75 micrometers. Most preferably, the recasted material can have an average height of about 40-60 micrometers.

With respect to the first objective, which is the formation of the primary cavity pattern, the desired pattern can be created using a software design tool, whereby the cavities have a target diameter range, which is otherwise referred to as length in this description. The primary cavities are preferably arranged to minimize the space between cavities, and this space can be an average of 5-20 micrometers in length. Although the design can be created for cavities to deliberately intersect and which are not precisely placed in a patterned arrangement to make the resulting surface look less organized and more "natural", this is not always necessary since there will also be a secondary cavity formation which will make the surface look more natural and further reduce the existence of smooth surfaces to improve osseointegration.

Figure 12:
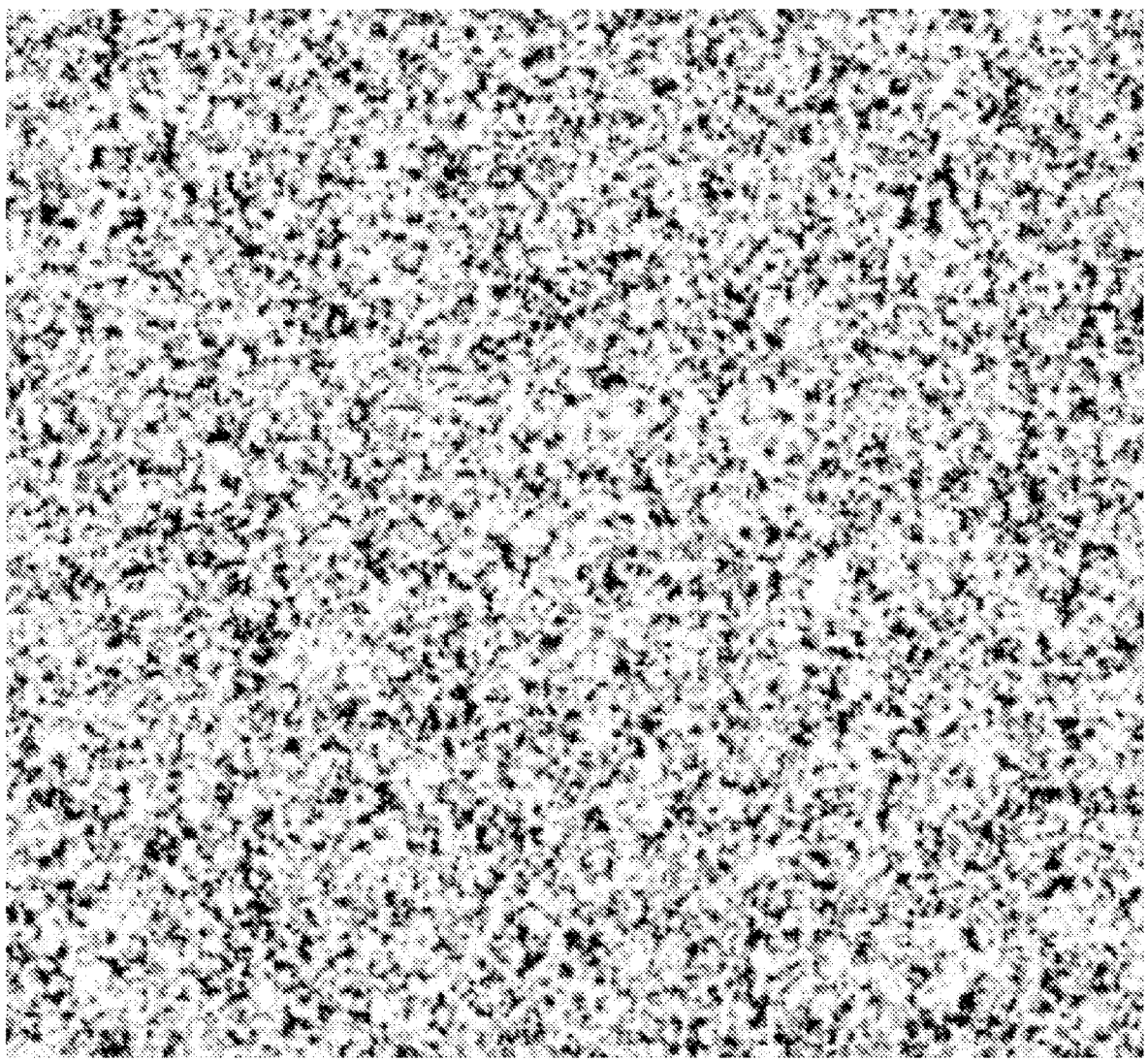
FIG. 12 shows a close-up view of a pattern of secondary cavities formed on a substrate.

The secondary cavity pattern is formed by one or more passes of the laser with potentially different laser parameters from the formation of the primary cavities to achieve the desired secondary cavity pattern of secondary cavities. The secondary cavities are smaller than the primary cavities and may be present between the primary cavities and inside the primary cavities, resulting in an increase in cavity surface and a decrease in smooth surface, which improves the osseointegration of bone into the treated substrate. In some embodiments, the secondary cavity pattern can be a "randomized" pattern where software randomly determines the location of each secondary cavity on the pattern. FIG. 12 shows a "randomized" pattern of secondary cavities, whereby darker areas represent deeper cavity formation. Alternatively, in other embodiments, the software can make an "intelligent" pattern which is based on the primary pattern. For example, much of the smooth surface to be roughened by the secondary cavity pattern is inside or between the primary cavities. Accordingly, the secondary pattern could be created based on the primary cavity pattern to prioritize the formation of secondary cavities inside the primary cavities and in between the primary cavities. In fact, to save time and expense, the secondary cavity pattern could be designed to primarily or exclusively create secondary cavities inside the primary cavities and in between the primary cavities and excluding the recasted material or excluding the location around the cavities where the recasted material is likely to be present. This way, the secondary cavities would reduce smoothness inside the primary cavities and in the substrate surface without reducing the amount of recasted material around the cavities. Another option is to predetermine a pattern of secondary cavities and provide this information to the laser system which is creating the cavities. The predetermined pattern could merely be a grid of secondary cavities with a particular distance between the cavities.

In some embodiments, the secondary cavities have an average penetration (or depth) of between 2 nanometers to 15 micrometers. In other embodiments, the depth is between 5 nanometers to 10 micrometers. The secondary cavities can have an average width (or length) between 5 nanometers and 1 micrometer.

The creation of primary and secondary cavities, as mentioned above, is highly beneficial for implants, and especially spinal implants, as this assists in the rapid stabilization of the spine, recovery of the patient who received the implant, and the reduction of adverse effects from having foreign objects in a body since those objects have been incorporated as part of the body.

Reference will now be made in detail to embodiments of the present disclosure, examples of which are illustrated in the accompanying drawings. Wherever possible, the same reference numbers will be used throughout the drawings to refer to the same or like parts.

Figure 1:
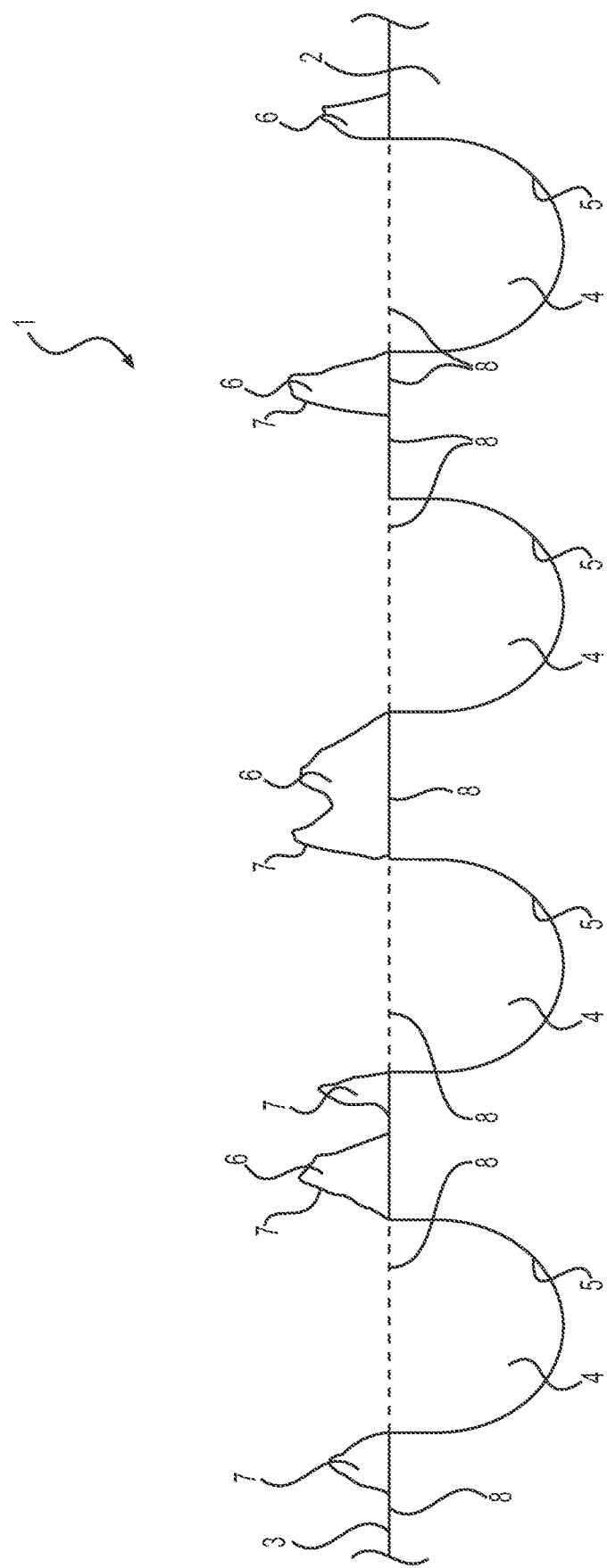
FIG. 1 shows a cross-sectional view of the primary cavity pattern of the present invention.

FIG. 1 shows a cross-sectional view of the primary cavity pattern 1 which is created by the laser pulses which preferably complete a number of passes in the formation of the primary cavities 4. The substrate 2 has a substrate surface 3 defining a substrate outer shape 8. The substrate outer shape 8 is the shape of the substrate surface prior to the formation of any primary cavities 4 or recasted portions 6. Once the primary cavities 4 are formed, the substrate outer shape 8 will be used to define a shape of the outer surface of the substrate as it would have existed without any primary cavities 4, recasted portions 6 (or secondary cavities 101 as described below). Below the substrate outer shape 8 are the etched primary cavities 4 having primary cavity surfaces 5. Above the substrate outer shape 8 are the recasted portions 6 which are formed adjacent or proximate to the cavities 4 and which have outer recasted surfaces 7. It is noted that recasted portions 6 are part of the primary cavity pattern 1 since they are, in some ways, an extension of primary cavities 4.

Figure 2:
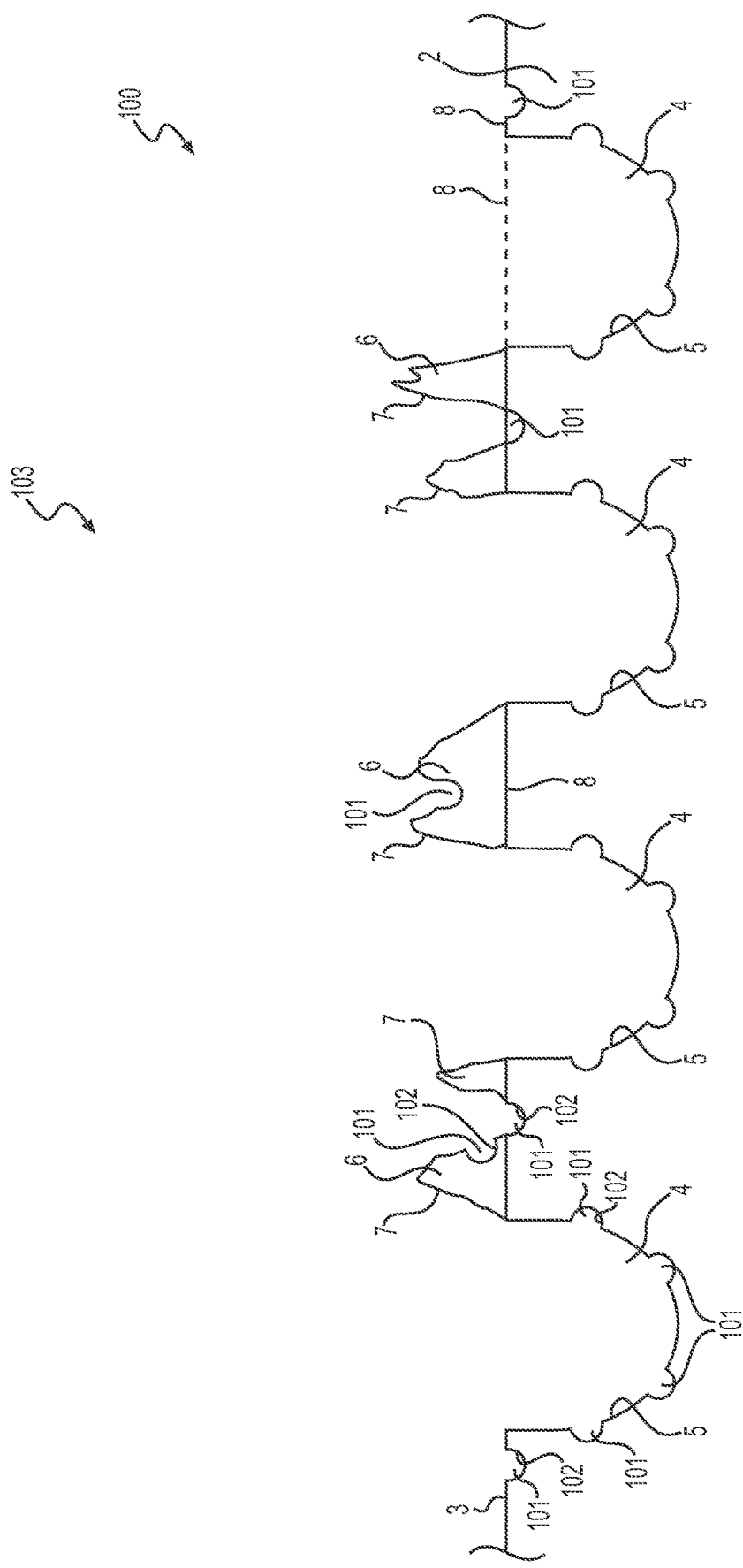
FIG. 2 shows a cross-sectional view of the combined primary and secondary patterns of the present invention.

FIG. 2 shows a cross-sectional view of the combined pattern 103 which is created by a combination of the primary cavity pattern 1 and the secondary cavity pattern 100 which is preferably created by the secondary set of laser passes. As mentioned above, the substrate 2 has a substrate outer shape 8. Below the substrate outer shape 8 are the etched primary cavities 4 having cavity surfaces 5. Above the substrate outer shape 8 are the recasted portions 6 which are formed adjacent or proximate to the cavities 4, and which have recasted surfaces 7. Additionally, there are secondary cavities 101 which are formed on the substrate surface 3, the primary cavity surfaces 5, and/or the recasted surfaces 7. The secondary cavity pattern 100 is the pattern of the secondary cavities 101, which overlaps with the primary cavity pattern 1. The combination of the primary cavity pattern 1 and the secondary cavity pattern 100 shall be referred to as the combined pattern 103. The secondary cavities 101 have secondary cavity surfaces 102. The secondary cavities 101 can be formed in the bottom of the primary cavities 4 as well as the sides of the primary cavities 4. Since the laser is can be incident from the top, in some embodiments, the secondary cavities 101 can be formed on the bottom of the primary cavities 4 rather than the sides of the primary cavities 4. In other embodiments, the secondary cavities 101 can be formed on the sides of the primary cavities 4.

FIG. 2 shows secondary cavities 101 on the sides of the primary cavities 4, in accordance with some embodiments. While the formation of the secondary cavities 101 reduces the amount of the recasted portions 6 by vaporizing material from recasted portions 6, much of the recasted portions 6 should still remain on the substrate 2 and their surface area may increase with the formation of secondary cavities 101. This will advantageously improve the osseointegration properties of the recasted portions 6. Also, as mentioned above, the secondary cavity pattern 100 can be predetermined to reduce the creation of secondary cavities 101 on recasted portions 6 by focusing more on the inside of the primary cavities 4 and on portions of the substrate 3 where there is likely to be no recasted portions 6, if desired. For simplicity, not all of the secondary cavities 101 or secondary cavity surfaces 102 were identified in FIG. 2.

Figure 3:
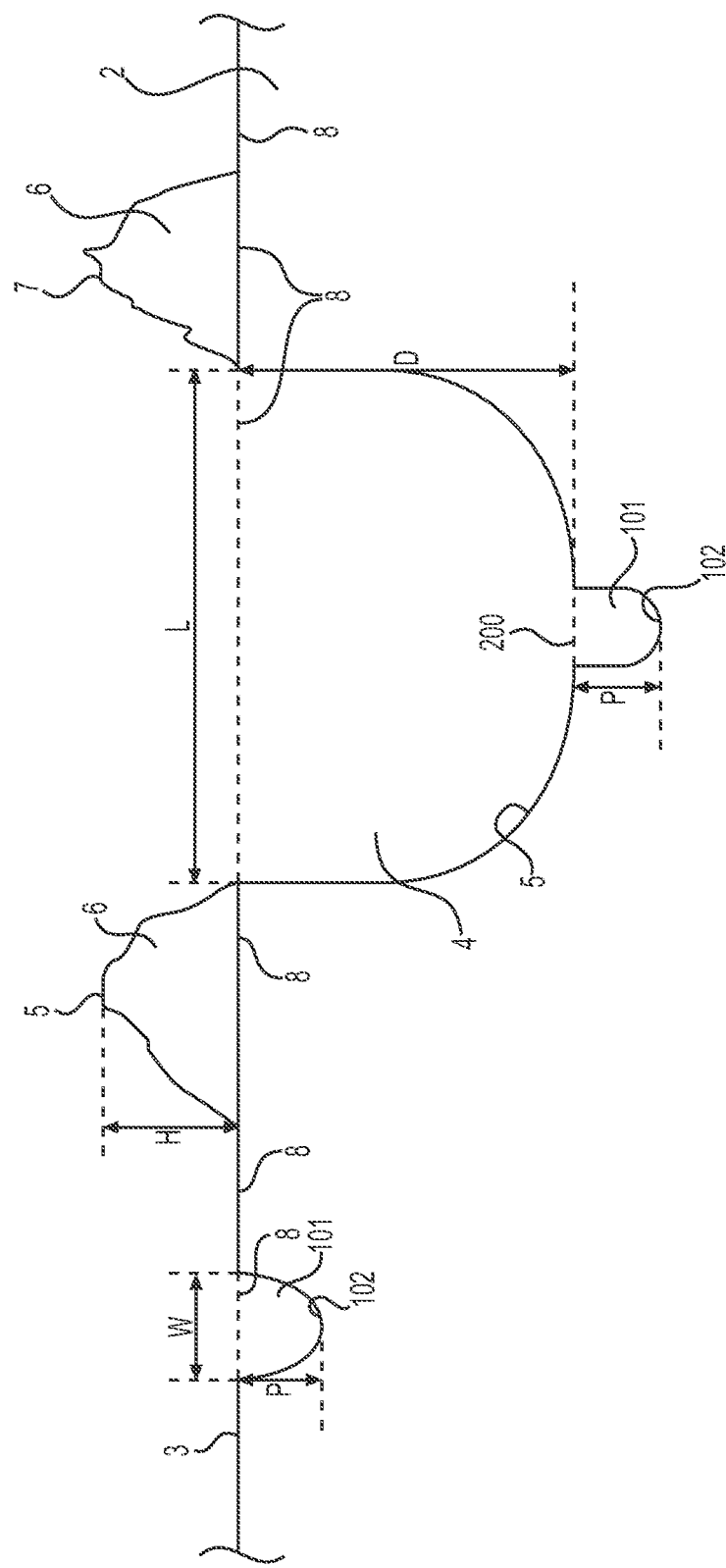
FIG. 3 shows an enlarged cross-sectional view of the cavity structure of the present invention.

FIG. 3 shows an enlarged cross-sectional view of the substrate 2 with one primary cavity 4, one secondary cavity 101, and recasted portions 6. The length L is the distance across a primary cavity 4 along the substrate surface 3. The etched depth D is the distance between the substrate outer shape 8 and the cavity inner shape 200 (as defined below). The height H of the recasted portion 6 is the distance between the substrate outer shape 8 and the recasted surface 7. The net depth ND is defined as the etched depth D plus the height H, thus, ND=D+H. The primary cavity 4 has a cavity surface 5 defining a cavity inner shape 200. The cavity inner shape 200 is the shape of the cavity surface 5 prior to the formation of any secondary cavities 101. Once the secondary cavities 101 are formed, the cavity inner shape 200 will be used to define a shape of the inner surface of the primary cavity 4 as it would have existed without any secondary cavities 101. If the secondary cavity 101 is inside the primary cavity 4, the penetration P of the secondary cavity 101 is the distance between the cavity inner shape 200 and the secondary cavity surface 102. If the secondary cavity 101 is on the substrate surface 3, then the penetration P of the secondary cavity 101 is the distance between the substrate outer shape 8 and the secondary cavity surface 102. The width W is the distance across a secondary cavity 101 along the substrate surface 3.

FIG. 4 shows a top view of primary pattern 1, including primary cavities 4, substrate surface 3, and recasted portions 6. Not all instances of primary cavities 4 are labeled as such due to the large number of the primary cavities 4. Also not all of the recasted portions 6 are shown due to the high number of recasted portions 6. The secondary cavities 101 are not part of the primary pattern 1 and some of the secondary cavities 101 are shown for clarification purposes of where they would be in a combined pattern 103. Not all of the secondary cavities 101 are shown due to the large number of secondary cavities 101 that would be present.

In some embodiments, primary cavities 4 are comprised of completely or substantially spherical cavities. In some embodiments, the primary cavities 4 can be individual spheres, or can be conjoined with neighboring spherical cavities. In some embodiments, all or a majority of the primary cavities 4 include a perimeter that has at least one rounded surface. In some embodiments, conjoined spherical cavities 4 can have a non-spherical bridge portion formed between them. In some embodiments, primary cavities 4 can assume a "dumbbell" shape appearance with rounded side surfaces and a bridge therebetween.

In some embodiments, secondary cavities 101 are formed in and around the primary cavities 4 on the substrate surface 3. In some embodiments, the secondary cavities 101 can include spherical and non-spherical surfaces. In some embodiments, while the primary cavities 4 can be deliberately formed to include the pattern as shown in FIG. 4, whereby all or more of the primary cavities 4 include spherical surfaces, the smaller, secondary cavities 101 will be more randomized. By applying such a technique, the primary cavities 4 provide a desired structure, while the secondary cavities 101 provide a desired texture, thereby promoting osseointegration on the substrate surface 3.

Figure 5:
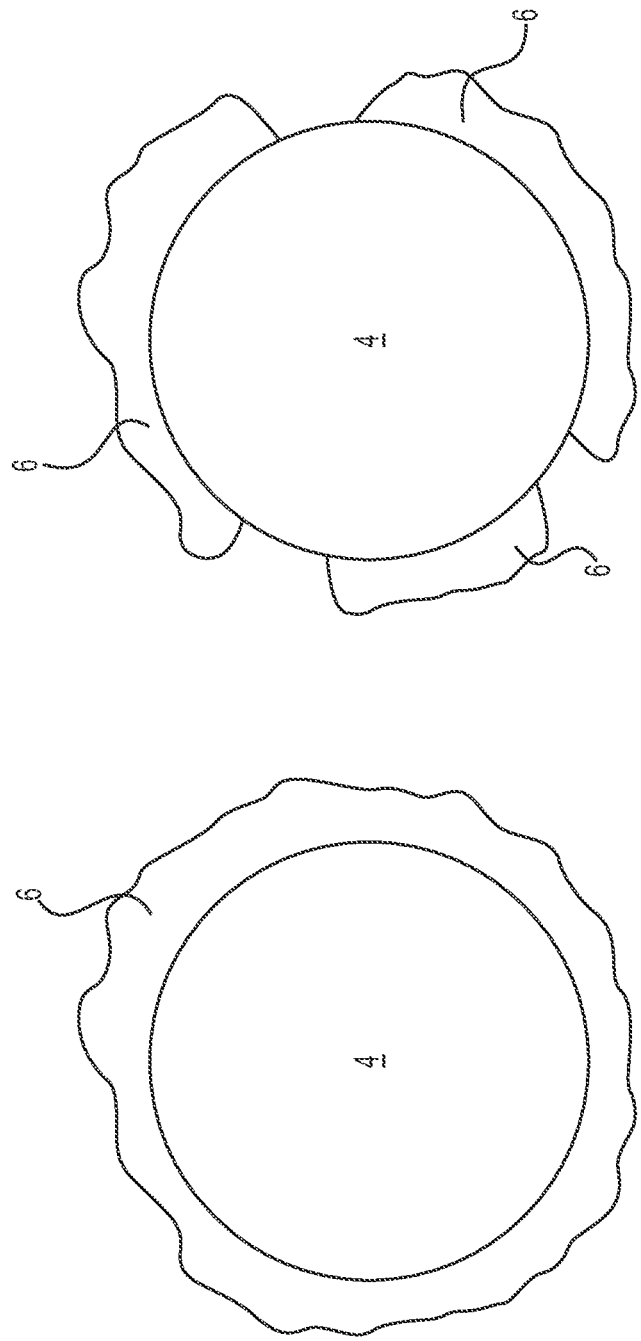
FIG. 5 shows a top view of two primary cavities of the present invention.

FIG. 5 shows a top view of two primary cavities 4 side-by-side. One primary cavity 4 is partially surrounded by the recasted portion 6 and one primary cavity 4 is completely surrounded by the recasted portion 6. In the present invention, between 90-100% of the primary cavities 4 have recasted portions 6 adjacent to them. Between 85% and 100% of the primary cavities 4 have recasted portions 6 that completely encircle respective primary cavities 4. Also, between 80% and 100% of the primary cavities 4 have recasted portions 6 which encircle between 50% and 100% of the outer perimeter of respective primary cavities 4.

Figure 6:
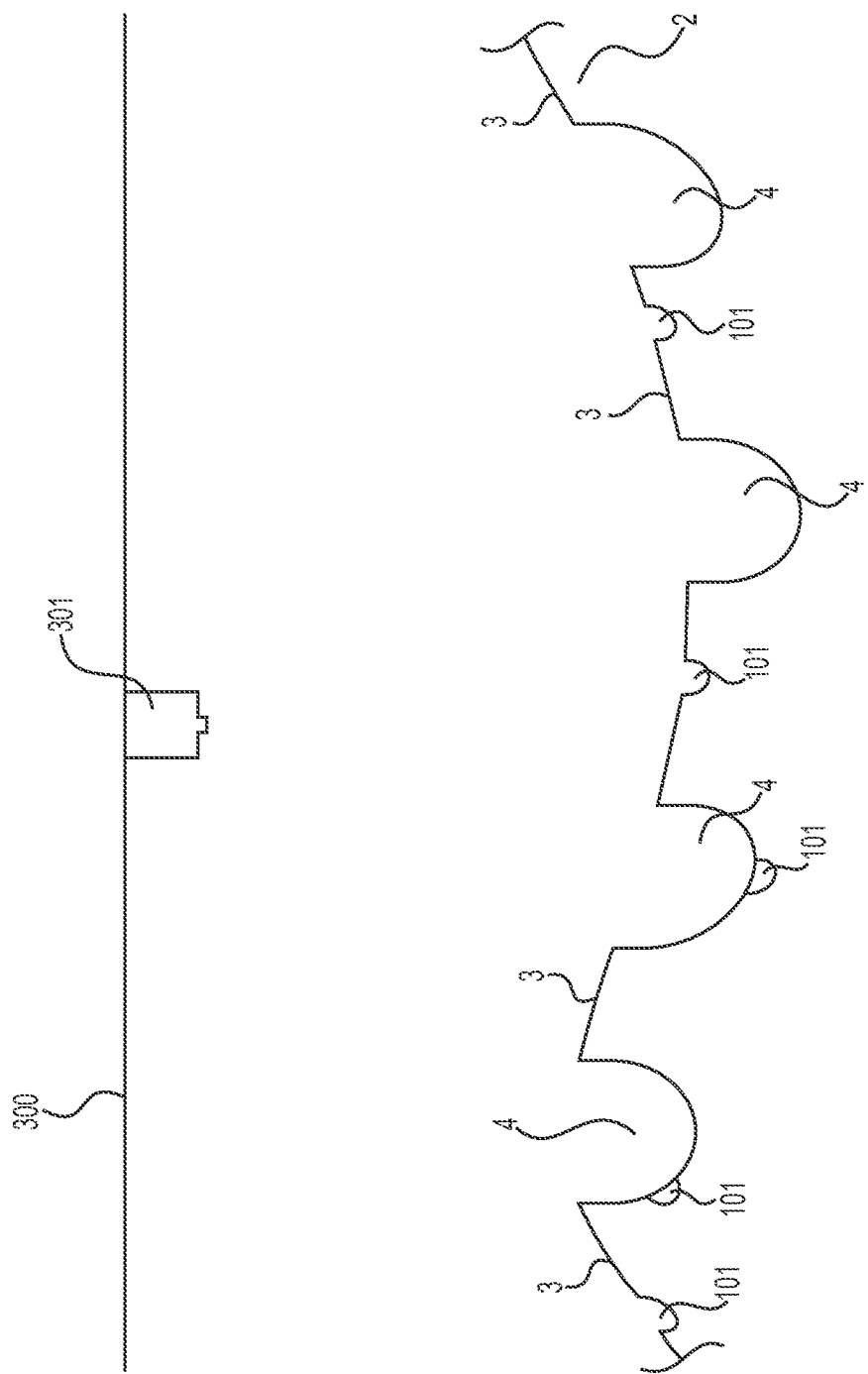
FIG. 6 shows a cross-sectional view of the substrate in which the orientation of the primary cavities and secondary cavities is shown.

FIG. 6 shows a side view of the substrate 2 in which the orientation of the primary cavities 4 and secondary cavities 101 is shown. The substrate 2 is shown with substrate surfaces 3 which are not flat in order to show the orientation of the cavities 4, 101. While the invention is not limited to this embodiment, in this situation the laser plane 300 is a plane perpendicular to the direction of the travel of the laser pulse. In practice, the laser 301 would move relative to the substrate 3 and/or the substrate 3 would move relative to the laser 301. Since the direction of travel of the laser pulses is perpendicular to the laser plane 300, all of the cavities 4, 101 would be aligned to the direction of travel of the laser beams and be formed perpendicular to the laser plane 300. The recasted portions 6 are omitted from FIG. 6 to simplify the figure. The advantage of this perpendicular orientation between direction of travel of the laser pulses and the laser plane is that this facilitates the ability to fire the laser 301 a number of passes to coincide with the primary cavity pattern 1 and/or secondary cavity pattern 100 in an efficient and timely manner. When doing multiple laser passes to form cavities, it is important to align the different laser pulses at different times with the same cavities 4, 101 to "build" a cavity 4, 101, which is of appropriate dimensions.

The above-described surface treatments can be applied to a number of substrates, including the outer surfaces of medical implants. In some embodiments, the surface treatments can be applied to spinal implants. A common procedure for handling pain associated with intervertebral discs in the spine that have become degenerated due to various factors such as trauma or aging is the use of intervertebral spacers to, e.g., fuse one or more adjacent vertebral bodies. Generally, to fuse adjacent vertebral bodies, the native intervertebral disc is first partially or fully removed. An intervertebral spacer is then typically inserted between neighboring vertebral bodies to maintain normal disc spacing and restore spinal stability, thereby facilitating an intervertebral fusion. In order to further support fusion, the intervertebral spacer preferably includes the surface treatment which is the subject of the present invention.

Figure 7:
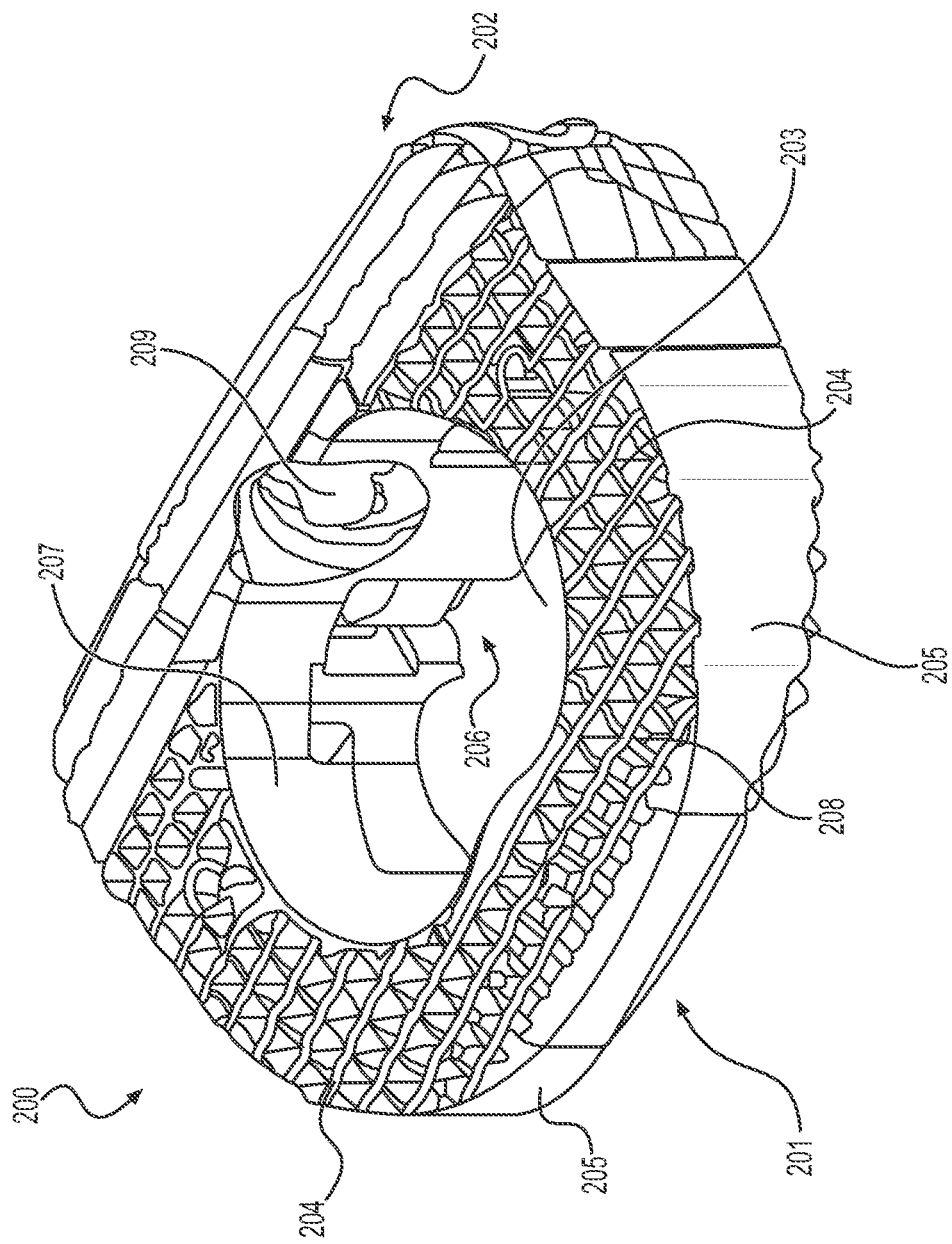
FIG. 7 shows an isometric view of a spacer according to the present disclosure.

FIG. 7 illustrates an example of an intervertebral spacer 200 insertable into a disc space according to the present disclosure. The intervertebral spacer 200 as shown in FIG. 7 may be, e.g., a stand-alone anterior lumbar interbody spacer used to provide structural stability in skeletally mature individuals following discectomies. These intervertebral spacers may be available in various heights and geometric configurations to fit the anatomical needs of a wide variety of patients. Specifically, FIG. 7 illustrates one embodiment of an intervertebral spacer 200. Intervertebral spacer 200 may be generally positioned in the intervertebral space between two adjacent vertebral bodies. As shown in FIG. 7, intervertebral spacer 200 may include a spacer portion 201 and a plate portion 202. In one example, the spacer portion 201 may include a graft window 203 for the placement of, e.g., bone graft or bone-growth inducing material 206, to enhance fusion between two adjacent vertebral bodies. The graft window is defined by a window surface 207, which includes inside surfaces of the spacer portion 201 and plate portion 202. The spacer portion includes a top portion 204 and a lateral portion 205.

The spacer portion 201 can be comprised of any material that is conducive to the enhancement of fusion between the two adjacent vertebral bodies. In the present invention, the spacer portion 201 is made of metal. The spacer portion 201 further may include top surface 204 and opposed bottom surface that are provided with a plurality of geometric configurations, such as, e.g., protrusions 208 (e.g., ribs, bumps, other textures, or the like). The protrusions 208 can be configured to be any size or shape for further anchoring the spacer portion 201 to each of the adjacent vertebral bodies. Protrusions 208 on the superior surface 204 and the inferior surface may grip the endplates of the adjacent vertebral bodies to aid in expulsion resistance. Protrusions 208 are of much larger size than the cavities of the present invention and may contain such cavities to enhance osseointegration.

The surface treatment of the present invention can be imparted on any surface (including any protrusions 208, if present on the surface) of the intervertebral spacer 200, including the spacer portion 201 and the plate portion 202. Spacer portion 201 can include surface treatment on the top surface 204, the bottom surface, on the spacer lateral portion 205, and on the window surface 207. For cost considerations, not all of the surfaces of the intervertebral spacer 200 may include the surface treatment of the present invention. Preferably, one or more of the top surface 204 and the bottom surface of the spacer 201, and the lateral portion 205, and the window surface 207 would have the surface treatment since they are instrumental in the bone growth and integration thereof. In particular, to save costs, the surface treatment could be on just the top surface 204 and the bottom surface of the spacer 201. Preferably, the surface treatment is present on 75%-100% of the top surface 204 and bottom surface of the spacer 201. The surface treatment can be present on 75% to 100% of any surface of the spacer 201, such as the top surface 204 and the bottom surface of the spacer 201 and still be very effective. When referring to a percent of surface treatment, this means the relative area which has been treated and the area includes cavities and spaces between cavities. As shown in FIG. 7, intervertebral spacer 200 may include one or more bores 209 for connecting the intervertebral spacer 200 with screws, or other fasteners, and the vertebrae. The screws can also be imparted with surface treatment to improve osseointegration.

Figure 8:
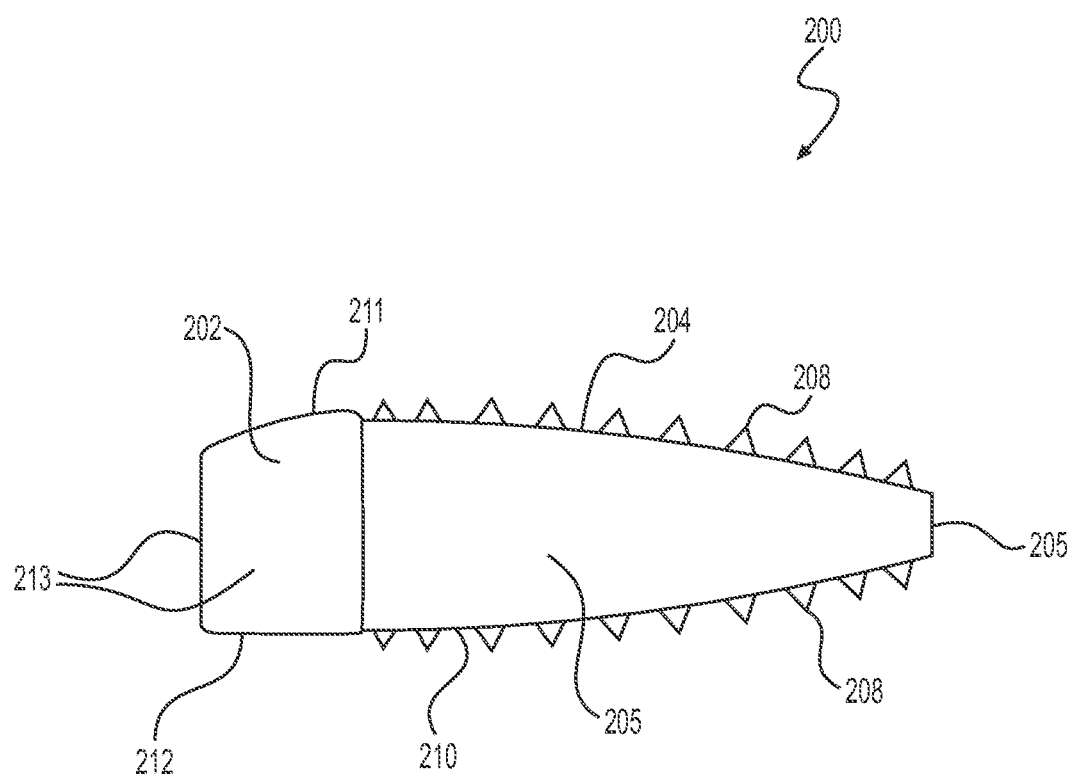
FIG. 8 shows a simplified side view of a spacer according to the present invention.

FIG. 8 shows a simplified side view of intervertebral spacer 200, including the spacer top surface 204, the spacer bottom surface 210, the spacer lateral portion 205, the protrusions 208, the plate portion 202, the plate portion lateral surface 213, the plate portion top surface 211, and the plate portion bottom surface 212. The surface treatment of the present invention can be utilized on one or more of the spacer top surface 204, the spacer bottom surface 210, the spacer lateral portion 205, the protrusions 208, the plate portion 202, the plate portion lateral surface 213, the plate portion top surface 211, and/or the plate portion bottom surface 212. As stated above, 75%-100% or 75% to 90% coverage with the surface treatment is desired for any particular surface. Also, to save costs, the surface treatment may be included only on spacer top surface 204 and spacer bottom surface 210.

Figure 9:
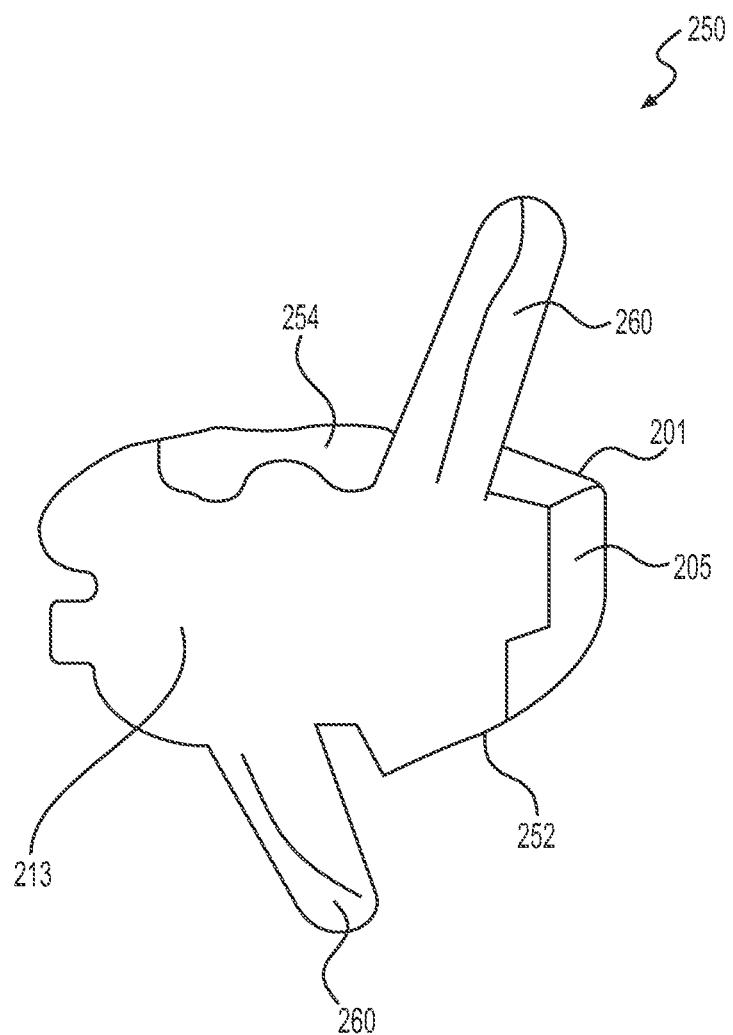
FIG. 9 illustrates an attachment mechanism according to the present invention.

FIG. 9 illustrates an attachment mechanism for an intervertebral spacer 250 which includes curved anchors 260 that can be used in conjunction with screws or in lieu of screws. In some embodiments, this attachment system can be part of the plate portion 252 and the curved anchors 260 can be used to attach the intervertebral spacer 250 to existing discs. In this embodiment, the surface treatment can be at spacer top surface 254 and opposed spacer bottom surface. The surface treatment can also be included in the attachment system, including the curved anchors 260, though this would be more expensive and may be omitted.

Figure 10:
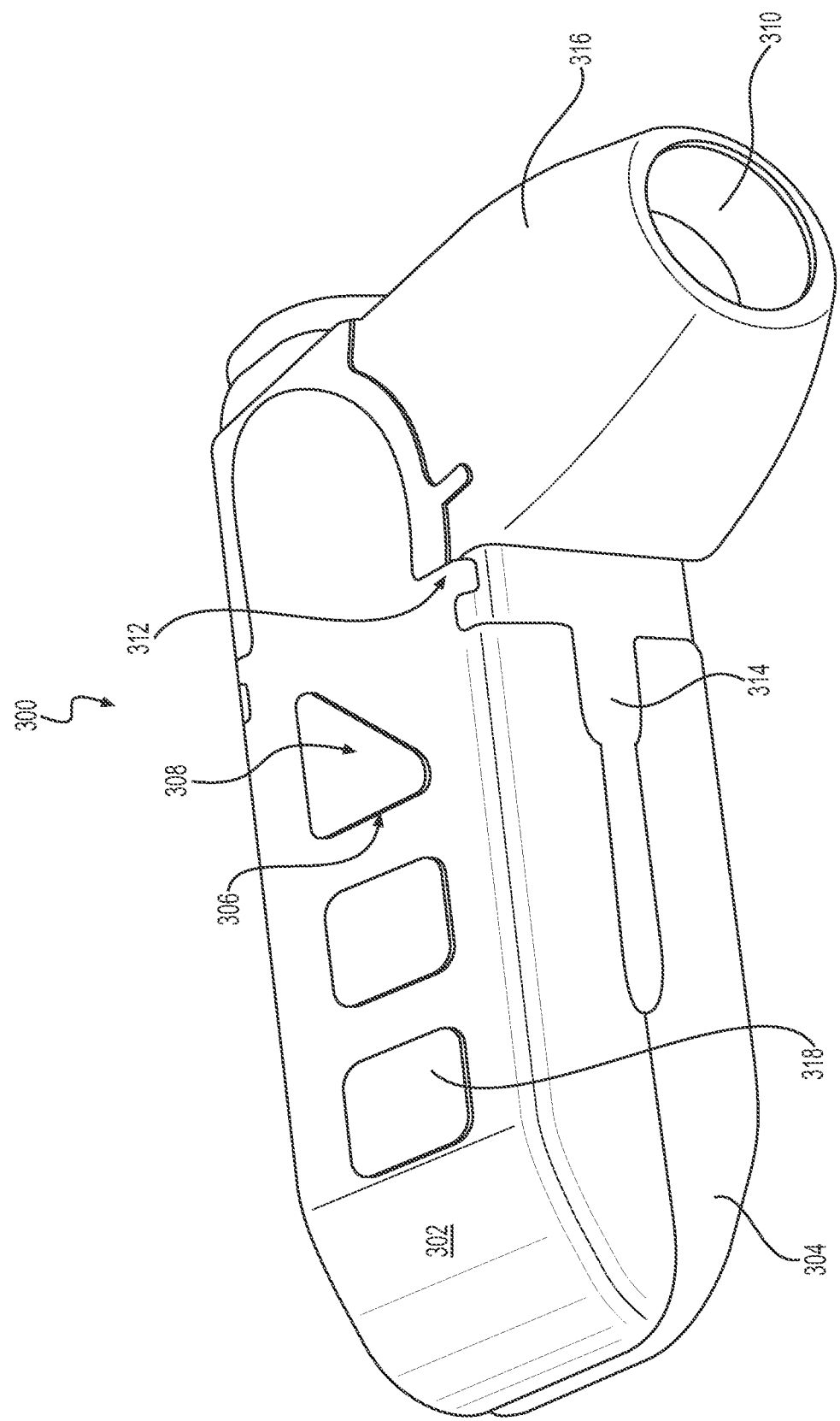
FIG. 10 shows an expandable spacer according to the present invention.

FIG. 10 shows an expandable spacer 300, which includes endplates 302, 304 having expansion ramps 306, mateable with moveable lift ramps 308 of a carriage. In the embodiment shown, endplates 302, 304 are symmetrical, and spacer 300 can be implanted with either endplate positioned superior with respect to the other. In other embodiments, they may be dissimilar, and a particular orientation may then be advantageous or necessary.

To expand spacer 300, lift ramps 308 are displaced relative to endplates 302, 304, causing expansion ramps 306 to slide along lift ramps 308, thereby moving endplates 302, 304 relatively apart, thereby increasing a height of spacer 300. Lift ramps 308 extend from a carriage, which is slideably retained within a frame extending between endplates 302, 304. The carriage is displaced relative to endplates 302, 304 by being pulled by a pin 318 connected to a link threadably connected to an actuating screw 310. One or more guide elements 312, associated with frame 314, can be provided to prevent endplates 302, 304 from moving along a longitudinal axis along with the carriage, thereby causing lift ramps 308 and expansion ramps 306 to be moved relative to each other, expanding or contracting spacer 300. The actuating screw 310 can be prevented from moving along a longitudinal axis thereof by a blocking flange. The actuating screw 310 is contained in articulating screw support 316.

In some embodiments, the surface treatment of the present invention can be applied to the endplates 302 and/or 304. In some embodiments, for cost considerations, it is envisioned that the surface treatment of the present invention can be applied only to endplates 302 and/or 304. However, in other embodiments, the surface treatment of the present invention can be applied to any surface of the spacer 300, thereby enhancing osseointegration throughout the implant. For example, the surface treatment can be applied to one or more of endplate 302, endplate 304, articulating screw support 316, actuating screw 310, and frame 314. The surface treatment can be applied to 80-100% of the surface area of each surface, such as 95% of the endplate 302, and 95% of end plate 304, and such as 80% of articulating screw support 316.

The present invention is also directed to a method or process of forming the surface treatment mentioned above. In an embodiment, one step in the present process is to predetermine the location of primary cavities on a substrate. In other words, a design program or other program can be used to determine the location and/or size of primary cavities on a surface of the substrate, such as a surface of an implant. The design can include the length and depth of the primary cavities, as well as their location relative to one another.

This design can then be connected to a laser system which will form the primary cavities on the substrate surface. The design may be created in a software that is capable of communicating with the laser system so that the laser system can form the cavities at the locations identified by the design. Thus, the laser system will fire lasers at the substrate to make the primary cavities in accordance with the design.

In some circumstances, it has been found that if too much energy is applied to a small section of the substrate in too short of a time, this can create localized heating which embrittles the substrate and adversely affects its structural characteristics. Also, lasers that are too strong will create cavities with edges and shapes which are less defined. Accordingly, the parameters of the laser system, including the maximum power, the frequency, and the raster rate, and the number of passes can be controlled within certain ranges to have an efficient and reliable formation of cavities without undue localized hearing and undue formation of cavities with poorly defined shapes and edges. In some embodiments, the laser has a 50 Watt, 200 ns pulse laser source.

Figure 11:
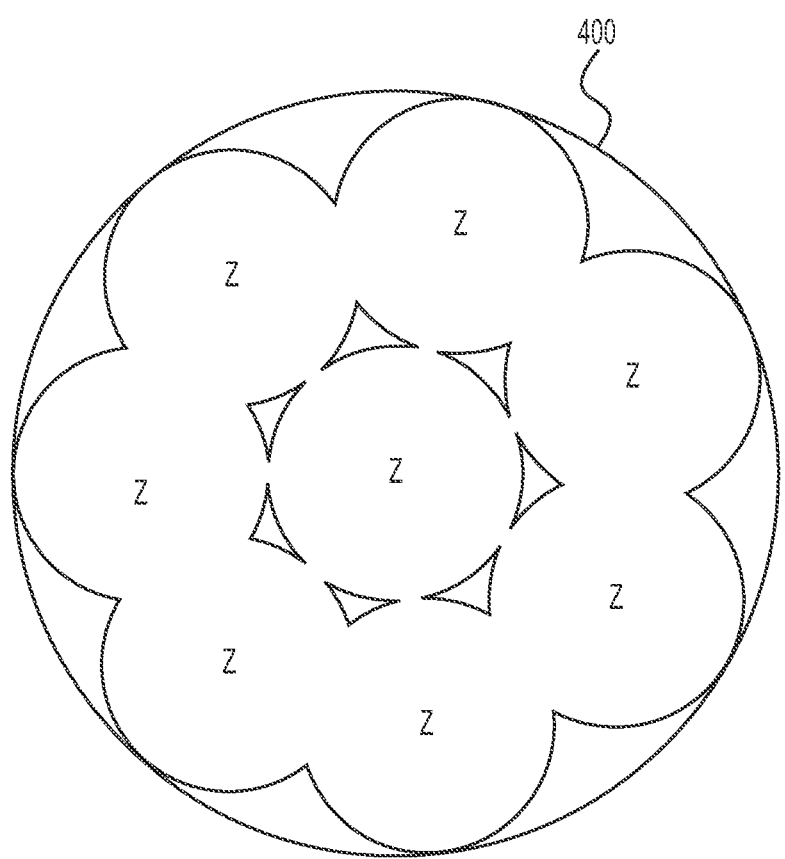
FIG. 11 shows a top view of a partial primary cavity.

In view of the above, the laser system will use laser pulses to form the cavities via one or more passes over the predetermined design. Thus, if the predetermined pattern has 3600 primary cavities, the laser system will fire one or more pulses on the location where the "first" cavity is desired. This will preferably form a partial cavity that has a length of 20-500 micrometers and 2-3 micrometers in depth. In one embodiment, to form the primary cavities, the power of the laser may be 1-50 watts. In another embodiment, to form the primary cavities, the power of the laser may be 40-50 watts. In yet another embodiment, the frequency of the laser (i.e., the frequency of the generation of laser pulses per unit time) is 50-200 kilohertz. In a further embodiment, the frequency of the laser is 25-500 hertz. The wavelength can be any wavelength suitable for lasers, such as an infrared laser having a wavelength of 1065 nanometers. The laser does not necessarily need to form the cavity in one pulse, and can fire multiple pulses to create the "first" partial cavity. For example, the laser may need 9 pulses to make the partial cavity with a length of 20-500 micrometers and the depth of 2-3 micrometers. FIG. 11 shows a partial primary cavity 400. If 9 pulses are fired to make the partial primary cavity 400, FIG. 11 shows 9 possible locations Z for the laser to be fired at the primary cavity 400. It is preferable to fire at different locations in order to achieve the desired length. The locations Z for the laser to be fired are also part of the predetermined design which is inputted into the laser system. Thus, once the laser is turned on and is creating pulses at the desired frequency, the laser "beam" is moved within the location of where the primary cavity is desired to form the partial cavity with multiple pulses.

Then, the laser system will fire one or more pulses on the location where the "second" cavity is desired. This will preferably make a cavity that has a length of 20-500 micrometers and 2-3 micrometers in depth. In this scenario, now there would be 2 cavities having a length of 20-500 micrometers and a depth of 2-3 micrometers. Then the laser system will fire one or more pulses on the location where the "third" cavity is desired. This process would be repeated until all 3600 partial primary cavities are formed having a length of 20-500 micrometers and a depth of 2-3 micrometers. This will end the first "pass" of the laser system. The laser can be turned off between the formation of each partial cavity to avoid firing a laser in locations between where the cavities are desired.

The second pass of the laser system can begin by firing one or more laser pulses to the location of the "first" partial cavity to deepen it an additional 2-3 micrometers. Now the "first" cavity has a length of 20-500 micrometers and a depth of 4-6 micrometers. This procedure would be followed for the remaining 3599 cavities to finish the second pass. A number of passes would be undertaken until the desired depth of the cavity is achieved.

As mentioned above, one challenge in the formation of the primary cavities is the generation of localized heating. The utilization of multiple passes to form the primary cavities ameliorates this issue since the material has time to cool between one pass and another pass. The desired number of passes to form the primary cavities is 5-120. As the laser pulses strike the substrate, some of the substrate material will vaporize and turn into gas, and some will sputter and deposit proximate to the cavities. This deposit is described above as the "recasted" material. One of the advantages of this invention is that the step of forming the primary cavities will also result in the formation of the recasted deposits, and therefore create a pit surface in two directions. By creating a pit structure in a direction into the substrate (i.e., the cavities) as well as away from the substrate (i.e., the recasted portions), the total surface roughness increases thereby improving osseocompatibility to a greater extent than a pit structure in only one direction. Since the same process creates the structure in two directions simultaneously, this is an efficient process to achieve osseocompatibility.

Once the primary cavities are completed, then the secondary cavities are formed by the laser. The secondary cavities are formed in the same way with a few differences. In some embodiments, the number of pulses for each pass for each partial secondary cavity is less than the partial primary cavities because the secondary cavities are smaller than the primary cavities. In some embodiments, there will also be more secondary cavities than primary cavities. Also, there are fewer passes needed to form the secondary cavities, with a desired range of 1-30 passes. The location of the secondary cavities can also be predetermined just like the location of the primary cavities.

Headings and subheadings, if any, are used for convenience only and do not limit the invention.

Any aspect set forth in any embodiment or example may be used with any other embodiment or example set forth herein. Every device and apparatus set forth herein may be used in a suitable medical procedure, such as, e.g., a vertebral disc replacement procedure, and may be advanced through any suitable body lumen, body cavity, or incision.

It will be apparent to those skilled in the art that various modifications and variations can be made in the disclosed products and processes without departing from the scope of the disclosure. Other examples of the disclosure will be apparent to those skilled in the art from consideration of the specification and practice of the disclosure disclosed herein. It is intended that the specification and examples be considered as exemplary only and that the present invention is not limited to the details shown. It is expressly intended, for example, that all ranges broadly recited in this document include within their scope all narrower ranges and points which fall within the broader ranges.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. Furthermore, to the extent that the term "include," "have," or the like is used in the description or the claims, such term is intended to be inclusive in a manner similar to the term "comprise" as "comprise" is interpreted when employed as a transitional word in a claim.

The invention claimed is:

1. A method for stabilizing a spine comprising the steps of:
providing a surgical implant comprising:
an implant body sized to be implanted in a patient and adapted to be in contact with a bone of the patient, the implant body having a surface treated outer surface, the outer surface containing a plurality of primary cavities and a plurality of secondary cavities smaller than the primary cavities,
wherein the outer surface comprises recast material adjacent to the primary cavities;
wherein the recast material has an average height of 1-100 micrometers, the primary cavities have an average depth of 19-499 micrometers from a surface of the implant, and the secondary cavities have an average depth of 5 nanometers to 10 micrometers.
positioning the surgical implant on a portion of the spine.

2. The method of claim 1, wherein the primary cavities have an average length ranging from 20-500 micrometers.

3. The method of claim 1, wherein the recast material is adjacent to at least 80% of the primary cavities, and wherein the recast material encircles the entire perimeters of at least 50% of the primary cavities.

4. The method of claim 1, wherein, the primary and secondary cavities are laser-formed cavities.

5. The method of claim 1, wherein one or more of the primary cavities is formed of two or more conjoined spherical portions.

6. The method of claim 1, wherein the surgical implant is a spinal implant selected from a group consisting of: an expandable spacer, a plate and spacer system, an implant with a screw system, an occipito-cervico-thoracic stabilization system, a cervico-thoracic stabilization system, and a plate system.

7. A method for stabilizing a spine comprising the steps of:
providing a surgical implant comprising:
an implantable body formed at least in part of a metal sized and configured to be inserted in a disc space, the body having an upper surface and a lower surface, wherein at least one of the upper surface and the lower surface includes a surface treatment which contains primary cavities and secondary cavities, the primary cavities being larger than the secondary cavities and the primary cavities having an average length ranging from 20-500 micrometers,
wherein the surface treatment includes recast material adjacent to a plurality of the primary cavities,
wherein the recast material has an average height of 1-100 micrometers, the primary cavities have an average depth of 19-499 micrometers from a surface of the implant, and the secondary cavities have an average depth of 5 nanometers to 10 micrometers;
positioning the surgical implant between adjacent vertebral bodies.

8. The method of claim 7, wherein the surgical implant is a spinal implant selected from the group consisting of: an expandable spacer, a plate and spacer system, an implant with a screw system, an occipito-cervico-thoracic stabilization system, a cervico-thoracic stabilization system, and a plate system.

9. The method of claim 7, wherein the implant is at least one selected from the group consisting of an expandable spacer and a plate and spacer system.

10. The method of claim 7, wherein the implant comprises a spacer and/or a plate, and wherein the surface treatment is present on both the upper surface and the lower surface of the body.

11. A method for stabilizing a spine comprising the steps of:
providing a surgical implant comprising:
an implantable body formed at least in part of a metal sized and configured to be inserted in a disc space, the body comprising an upper surface and a lower surface, wherein at least one of the upper surface and the lower surface comprises a surface treatment which contains primary cavities and secondary cavities, the primary cavities being larger than the secondary cavities,
wherein the surface treatment includes recast material adjacent to a plurality of the primary cavities,
wherein the recast material has an average height of 1-100 micrometers, the primary cavities have an average depth of 19-499 micrometers from a surface of the implant, and the secondary cavities have an average depth of 5 nanometers to 10 micrometers; and positioning the surgical implant between adjacent vertebral bodies.

12. The method of claim 11, wherein the upper and lower surface comprise the surface treatment.

13. The method of claim 11, wherein the implantable body is expandable.

14. The method of claim 11, wherein at least some of the primary cavities are spherical.

15. The method of claim 11, wherein at least some of the primary cavities are non-spherical.

16. The method of claim 14, wherein at least some of the primary cavities include two or more conjoined spheres.

17. The surgical implant of claim 14, wherein at least some of the primary cavities are barbell shaped with a bridge.

\* \* \* \* \*